(12) United States Patent
Ziegleder et al.

(10) Patent No.: US 8,082,772 B2
(45) Date of Patent: Dec. 27, 2011

(54) METHOD AND APPARATUS FOR PERIODICALLY MEASURING THE YIELD POINT OF DISPERSIONS, AND USE THEREOF

(75) Inventors: Gottfried Ziegleder, Munich (DE); Alexander Beaury, Grassau (DE)

(73) Assignee: Fraunhofer-Gesellschaft zur forderung der Angewandten Forschung e.V., Munich (DE)

( * ) Notice: Subject to any disclaimer, the term of this patent is extended or adjusted under 35 U.S.C. 154(b) by 351 days.

(21) Appl. No.: 12/306,149

(22) PCT Filed: Jul. 13, 2007

(86) PCT No.: PCT/EP2007/006257
§ 371 (c)(1),
(2), (4) Date: Feb. 20, 2009

(87) PCT Pub. No.: WO2008/011996
PCT Pub. Date: Jan. 31, 2008

(65) Prior Publication Data
US 2009/0151431 A1    Jun. 18, 2009

(30) Foreign Application Priority Data
Jul. 25, 2006   (DE) .................. 10 2006 034 346

(51) Int. Cl.
*G01N 11/00* (2006.01)
*G06F 15/00* (2006.01)
(52) U.S. Cl. ................................ 73/54.22; 702/127
(58) Field of Classification Search .............. 73/54.22
See application file for complete search history.

(56) References Cited

U.S. PATENT DOCUMENTS

| | | | | |
|---|---|---|---|---|
| 2,747,399 A | * | 5/1956 | Foreman ...................... | 73/54.15 |
| RE34,754 E | * | 10/1994 | Dickinson et al. ............... | 166/64 |
| 5,777,212 A | * | 7/1998 | Sekiguchi et al. ........... | 73/54.33 |
| 6,203,831 B1 | * | 3/2001 | Eder et al. ..................... | 426/103 |
| 6,912,891 B2 | * | 7/2005 | Coupland et al. ............ | 73/64.53 |

FOREIGN PATENT DOCUMENTS

| | | |
|---|---|---|
| DE | 241646 A1 | 10/1985 |
| DE | 3611867 | 10/1987 |
| DE | 290950 A5 | 9/1989 |
| DE | 19515250 | 7/1996 |

OTHER PUBLICATIONS

Bostwick Consistometer, 2003, CSC Scientific Company, Inc. (supplied by applicant).*

(Continued)

*Primary Examiner* — Hezron E Williams
*Assistant Examiner* — Gregory J Redmann
(74) *Attorney, Agent, or Firm* — Barnes & Thornburg LLP

(57) ABSTRACT

Methods and apparatus for measuring the yield value of flowable material in a flow of flowable material comprise iteratively wetting a measuring body by the flowable material at a relatively constant temperature, subsequently permitting the flowable material to discharge for a discharge time so that the measuring body achieves approximately constant weight, using a functional unit in communication with the measuring body to determine a residual quantity of the flowable material which adheres to the measuring body after the discharge time, and determining the yield value of the flowable material based upon the quantity of the flowable material adhering on the measuring body.

26 Claims, 5 Drawing Sheets

OTHER PUBLICATIONS

Figure 1:
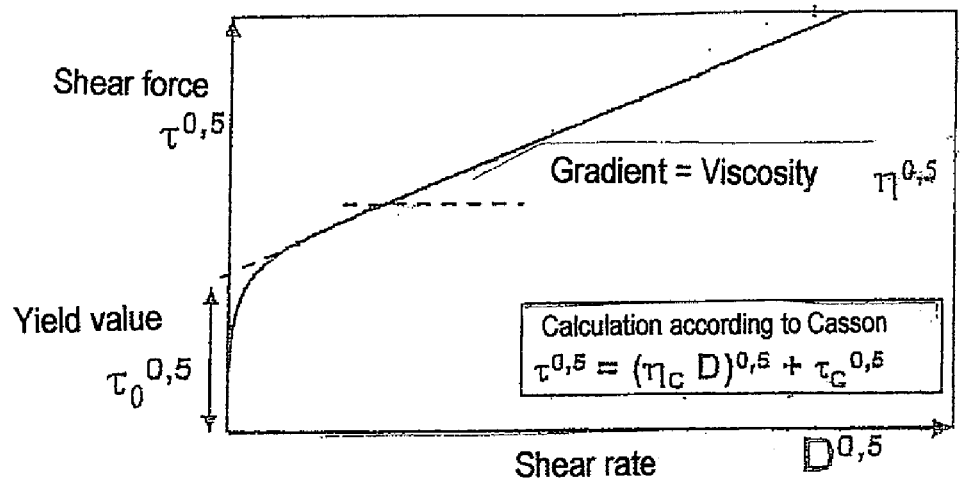

International Search Report/Written Opinion for PCT/EP2007/006257 completed Oct. 15, 2008.
International Confectionery Association, "Viscosity of Cocoa and Chocolate Products", *Analytical Method*, vol. 46, pp. 1-17.
Coussot, Philippe, et al., "Determination of Yield Stress Fluid Behavior from Inclined Plane Test", 1995, *Rheol Acta*, vol. 34, pp. 534-543.
Coussot, Philippe, et al., "Avalanche Behavior in Yield Stress Fluids", Apr. 20, 2002, *American Physical Society*, vol. 88, No. 17, pp. 175501-1/175501-4.
Becket, Stephen T., "The Science of Chocolate" 2000, *The Royal Society of Chemistry*, pp. 112-113, 133-134.
Bostwick Consistometer, 2003, CSC Scientific Company, Inc.
Windhab, Erich J., "Structure-Rheology Relationships in Chocolate Processing", Apr. 2011 & Dec. 1997, Confectionery Science, Proceedings of an International Symposium, Department of Food Science, College of Agricultural Sciences, Penn State University, pp. 104-126.

* cited by examiner

METHOD AND APPARATUS FOR PERIODICALLY MEASURING THE YIELD POINT OF DISPERSIONS, AND USE THEREOF

CROSS REFERENCE TO RELATED APPLICATIONS

This application is the U.S. national phase of PCT/EP2007/006257 filed Jul. 13, 2007. PCT/EP2007/006257 claims benefit under the Paris Convention to DE 10 2006 034 346.8 filed Jul. 25, 2006. The disclosures of both of DE 10 2006 034 346.8 and PCT/EP2007/006257 are hereby incorporated herein by reference.

The present invention describes a method and a device for measuring the yield value of flowable materials, a measuring body being wetted periodically by the flowable material to be measured. Furthermore, a use of the device is indicated.

High-viscous dispersions display non-Newtonian flow behaviour, i.e. in addition to a specific viscosity of the moving mass, they also have a yield value of the mass. This yield value, to be understood as internal friction of the dispersed particles in dense packing, must be overcome firstly in order to move the mass from the stationary state and to keep it moving.

The flow behaviour of chocolate masses is examined and measured, according to official methods (OICCC), in the melt at 40° C. Viscosity and yield value are thereby distinguished. Nowadays, rheometers are used for measurement in the range of a shear gradient between approx. 0 and 200 $s^{-1}$. During continuous passage of a rising or falling shear gradient in this range, a so-called flow curve is recorded, which represents the shear force over the shear rate.

The measurement and evaluation of flow curves of molten chocolates at 40° C. is described extensively in the literature (for example J. Chevalley, Die Fließeigenschaften von Schokolade (The Flow Properties of Chocolate), in: S. T. Beckett: Moderne Schokoladentechnologie (Modern Chocolate Technology), Behr Press 1990, pp. 211-231; H. D. Tscheuschner, Schokolade, Süßwaren (Chocolate, Confectionery), in: D. Weipert, H. D. Tscheuschner, E. Windhab, Rheologie der Lebensmittel (Rheology of Foods), Behr Press 1993, pp. 431-470; H. D. Tscheuschner, Rheologische Eigenschaften von Schokoladenmassen und deren prozessrelevanten Bedeutung (Rheological Properties of Chocolate Mass and the Process-Relevant Meaning thereof), Zucker- und Süßwarenwirtschaft (ZSW) (Sugar and Confectionery Industry) 1993, 136-147; Windhab E., Rolfes L., Messung des Fließverhaltens von Schokoladenmassen (Measurement of the flow behaviour of Chocolate Masses) ZSW 1991, 401). The evaluation of flow curves and approximate calculation of the yield value has been effected to date according to Casson untersuchungsmethoden des Office International du Cacao et du Chocolat, Methode Blatt (Examination Methods of the Office International du Cacao et du Chocolat, method sheet 10-D/1973, Viskosität von Schokolade—Bestimmung der Casson-Fließgrenze und der Casson Viscosität (Viscosity of Chocolate—determination of the Casson yield value and the Casson viscosity) (Glättli Press, postcode CH-6934 Bioggio (Switzerland)) and in a new version according to Windhab (International Confectionery Association, "Viscosity of Cocoa and Chocolate Products"; Analytical Method 46, pp. 1-17, ICA, rue Defacqz 1, 1000 Brussels (Belgium), Bestimmung der dynamischen Viscosität (Determination of the Dynamic Viscosity)). Possible other approximation methods for the yield value were discussed elsewhere (Windhab E. Structure-Rheology Relationships in Chocolate Processing, in: G. R. Ziegler: Confectionery Science, Proceedings Penn State University 1997, Dep. Food Science, 104-126). The principle of a yield value in general is described in two further publications (Coussot P., Boyer S. Determination of yield stress fluid behaviour from inclined plane test, Rheol. Acta 34: 534-543 (1995); Cousset P. Avalanche behaviour in yield stress fluids, Physical Review Letters, Vol. 88, No. 17, 175501-175504, (2002)) and is clarified in FIG. 1.

A simple adhesion quantity test for chocolate masses and chocolate coatings is known from the literature (J. Kleinert: Handbuch der Kakaoverarbeitung und Schokoladeherstellung (Handbook of Cocoa Processing and Chocolate Production), Behr Press, 1997, p. 402 ff.). However the represented method can only be implemented manually and is not suitable for a quasi continuous monitoring of chocolate melts. A further disadvantage of the method is that the method control there is configured very laboriously since the test bodies used must be firstly cooled after the wetting with the chocolate mass in order to determine the adhering residual adhesion quantity. In addition, a complex multiple determination is prescribed.

The principle of the inclined plane is described in various publications (Coussot P, Boyer S, Determination of yield stress fluid behaviour from inclined plane test. Rheol. Acta 34: 534-543 (1995); Cousset P. Avalanche behaviour in yield stress fluids, Physical Review Letters, Vol. 88, No. 17, 175501-175504, (2002); W. Bartusch, Der Einfluss von Rüttelstößen auf die Fließeigenschaften von Schokoladenmassen (The Influence of Vibrations on the Flow Properties of Chocolate Masses). Fette Seifen Anstrichmittel 63 (1961) 721-729; A. Beaury, Semester dissertation Fraunhofer IVV/FH Weihenstephan, in preparation, 2006). The yield value can be measured and calculated by means of the flow behaviour of a chocolate mass from a defined surface. The test surface can thereby be inclined diagonally at a specific angle α ("inclined plane") or stand perpendicularly (α=90°). Either the angle $α_1$ is determined at which the mass just begins to flow or the mass is determined which remains on the surface after conclusion of the flow process at the given angle α>$α_1$. The measuring method with a perpendicular testing plate and determination of the residual mass was used for the first time by Bartusch in statistical laboratory tests at 40° C. in order to test the effect of chocolate melts. Simple discharge funnels which are described in a further publication (S. T. Beckett, The Science of chocolate, RSC Paperbacks, ISBN 0-85404-600-3, p. 112) or the Bostwick Consistometer (Bostwick Consistometer, CSC Scientific Company Inc., 2003) likewise function according to the discharge principle on an inclined plane, but measure the rate of discharge and hence detect the viscosity and not the yield value.

For a wetted inclined plane or inclined surface with an angle of inclination α, the following equation applies for calculating the yield value τ

$$\tau = \frac{m \cdot g \cdot \sin\alpha}{A}$$

with: A=wetted surface
α=angle of inclination
m=mass of the residual adhesion quantity
g=acceleration 9.81 m/s²
For perpendicular surfaces of the measuring bodies (α=90°

C. and hence sin α=1), there applies correspondingly:

$$\tau = \frac{m \cdot g}{A}$$

It is therefore the object of the present invention to provide a simple method and a device with which a quasi continuous determination of the yield value of dispersions can be effected in a simple and reproducible manner. It is a further object of the invention to cover as wide a spectrum as possible of flowable materials by means of the measuring method.

According to the invention, a method for measuring the yield value of flowable materials in a flow of the respective flowable material is provided, a measuring body being wetted iteratively by the flowable material to be measured at a given, constant temperature, subsequently the flowable material being allowed to discharge partially for a prescribed discharge time which is calculated such that the measuring body approximately achieves a constant weight and the yield value being determined via the remaining residual adhesion quantity on the measuring body.

The selection criterion for the discharge time is thereby that the discharge time is calculated such that the measuring body approximately achieves a constant weight. There is thereby understood according to the invention that the relevant change in weight of the measuring body is thereby<1% per second. Generally the discharge time depends upon the viscosity of the flowable material to be measured. The more viscous the material to be measured the longer is the discharge time also.

Figure 2:
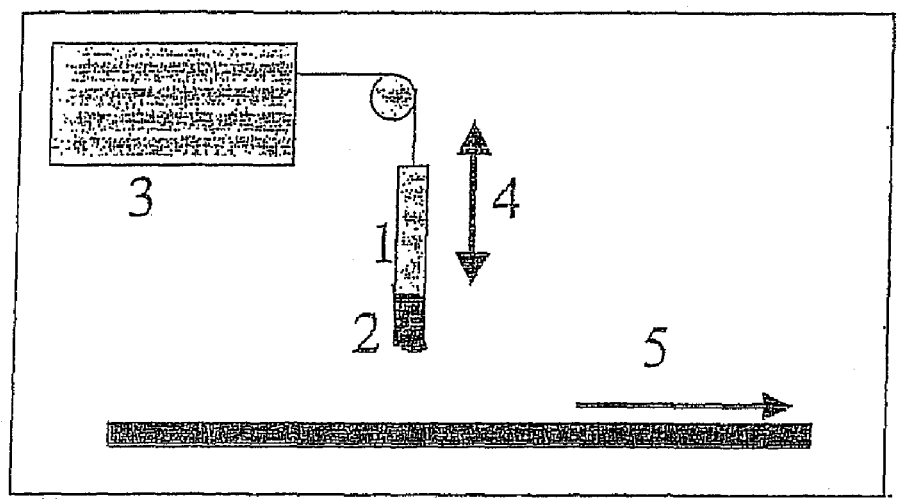

On the one hand, the measuring method can be effected such that the measuring body is immersed in the flowable material and is withdrawn again. This principle is illustrated in FIG. 2.

As an alternative embodiment, the measuring body is thereby drenched with the flowable material. This embodiment is reproduced by means of FIG. 3.

Figure 4:
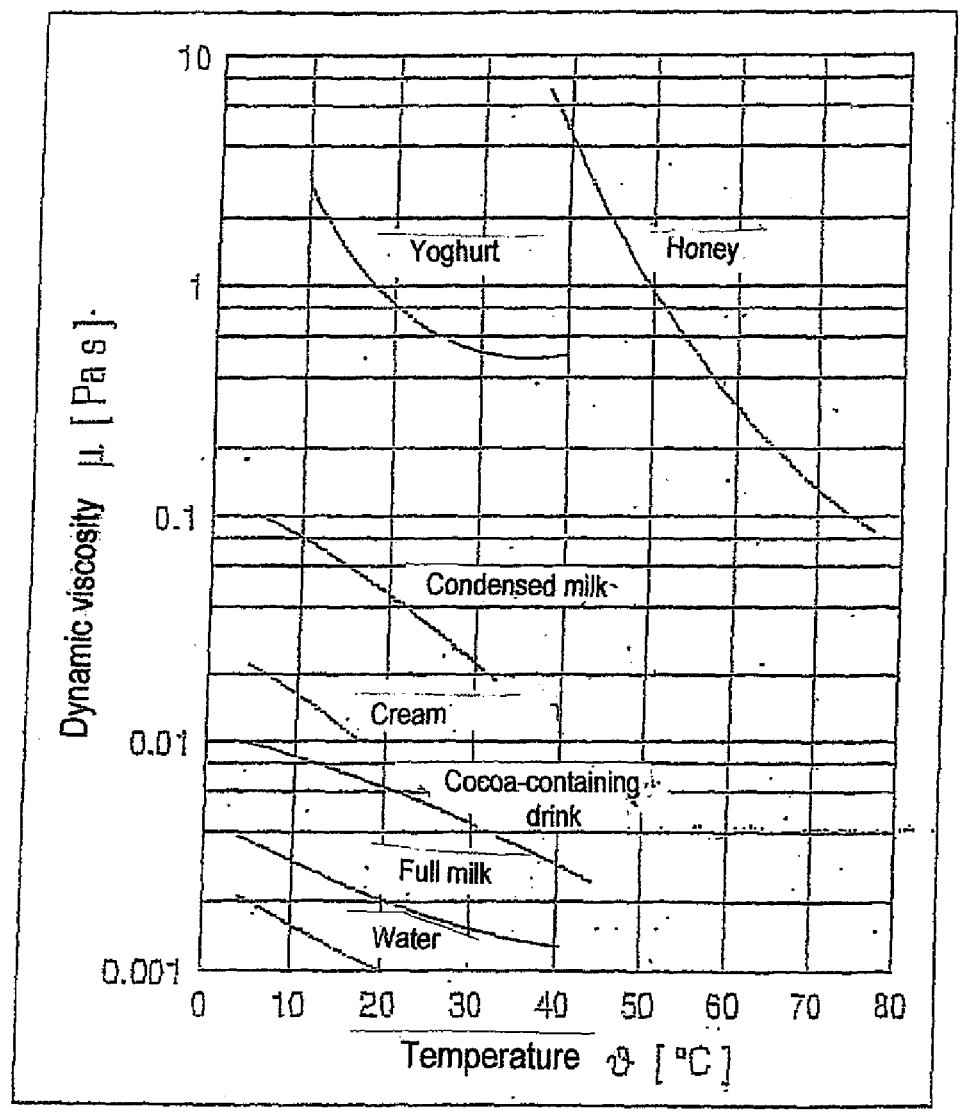

In every case, the time of immersion or drenching of the measuring body is chosen as a function of the viscosity of the flowable material to be measured and is calculated such that complete wetting of the measuring body and/or complete exchange of the flowable material are ensured. Different times are thereby required according to the flow behaviour of the material to be measured. These move in the case of low-viscous materials at a dynamic viscosity of for example 1 mPas to 1 Pas in the range of 10 s to 30 s, in the case of higher-viscous materials at a viscosity in the range of for example 1 Pas to 100 Pas with the order of magnitude of 30 s to 300 s without wishing to restrict the immersion times to the indicated times. An important advantage of the method is thereby that it is ensured due to the chosen immersion times that the adhering residual adhesion quantity is completely exchanged and the measuring body is controlled to the same temperature as the flowable material to be examined. Table 1 provides by way of example an overview of the dynamic viscosities of a selection of dispersions, the yield value of which can be determined with the present method. FIG. 4 shows the dependency of the viscosities of various materials as a function of the temperature. It becomes clear by means of these facts that it is essential to adjust the measuring body to the same temperature as the material to be measured in order to keep the rheological properties thereof as constant as possible.

After partial discharge of the flowable material, determination of the weight and/or of the volume of the residual adhesion quantity of the flowable material which adheres to the measuring body is effected.

The determination of the weight and/or of the volume of the residual adhesion quantity is thereby effected advantageously via sensors, selected from the group comprising scales, force transducer, oscillation sensor, optical sensors, electromagnetic sensors, piezoelectric sensors and/or pressure transducers.

In a further advantageous embodiment of the method, vertical and/or inclined surfaces of the measuring body are wetted.

Advantageously, the method is implemented such that the adhering residual quantity during the measurement has virtually identical rheological properties to the flowable material from which it was removed. There are intended amongst these for example the dynamic viscosity, yield value and all the physical properties which depend upon the temperature. Due to the iterative, periodic immersion or drenching of the measuring body with the flowable material to be measured, this condition is ensured since a constant exchange of the flowable material is effected. As a result, it is also ensured that the measuring body always has the same temperature as the material to be measured and the measuring body hence does not contribute to falsifying the rheological properties of the material to be examined.

The further alternative embodiment also serves to ensure this condition further, in that the measuring body is tempered and/or drenched in the flowable material between two measuring cycles.

The determined measuring data are preferably further processed and/or stored electronically.

According to the invention, the dispersions to be measured can be selected from the group comprising viscous masses in the food or pharmaceutical field, cosmetics, dispersion paints and/or ceramic masses.

Dispersions from the food, cosmetic and/or pharmaceutical field can be selected for example from the group comprising chocolate melts, yoghurt, ketchup, sandwich spreads, jam and/or honey or creams, ointments, lotions, lipstick, etc.

The method is, surprisingly, particularly well suited in particular in the case of chocolate masses for determining in a simple manner the tempering degree, i.e. the degree of crystallisation of chocolate masses.

In a further preferred embodiment of the method, the measurement of the yield value is combined with a measurement of the temperature of the flowable material, i.e. the measuring parameters—for instance immersion and discharge time—are chosen according to the invention as a function of the temperature of the flowable material.

In particular if all the factors which determine crucially the rheology of the material to be measured are taken into account, a measurement of the yield value which is as precise, reproducible and reliable as possible is made possible. In particular the temperature has great influence on the dynamic viscosity and hence the rheology of the material to be measured. The dependence of the dynamic viscosity of selected materials is reproduced in FIG. 4.

According to the invention, a measuring device is likewise provided for the periodic measurement of the yield value of flowable materials, having a measuring body with a defined surface which is in communication with a functional unit for determining the adhering residual adhesion quantity of the flowable material which remains on the measuring body after the dropping time and a means for ensuring the periodic wetting of the measuring body with the dispersion.

In one embodiment, the means which is contained for ensuring the periodic measurement of the measuring body can be a lifting device for lowering and lifting the measuring body in or out of the flowable material.

In an alternative embodiment, the means is a device for separating a partial quantity of the flowable material and for diverting the partial quantity towards the measuring body. This can be for example a mechanical slide, a flap and/or a valve.

In principle, a measuring body can have any arbitrary form, e.g. the form of a rod, a plate, a funnel, a cone and/or a sphere.

Preferably, the measuring body should have vertical and/or inclined surfaces which are wetted by the flowable material.

The functional unit with which the residual quantity of adhering flowable material on the measuring body is determined is advantageously selected from the group comprising scales, force transducer, oscillation sensor, optical sensors, electromagnetic sensors, piezoelectric sensors and/or pressure transducers.

Advantageously, an electronic evaluation unit is provided in addition for further processing and/or storing the measuring data, preferably a computer.

The method is suitable for preference for continuous monitoring of flowable materials in a production plant.

The present invention is likewise suitable for determining the tempering degree, i.e. the degree of crystallisation of chocolate masses.

The present invention is intended to be explained in more detail with reference to the following Figures without intending that the invention is restricted to the embodiments shown there.

The principle of a yield value in general is described in two further publications and is illustrated in FIG. 1.

FIG. 2 describes the embodiment of the invention in which the measuring body is immersed in the flowable material to be measured by lifting and lowering.

Figure 3:
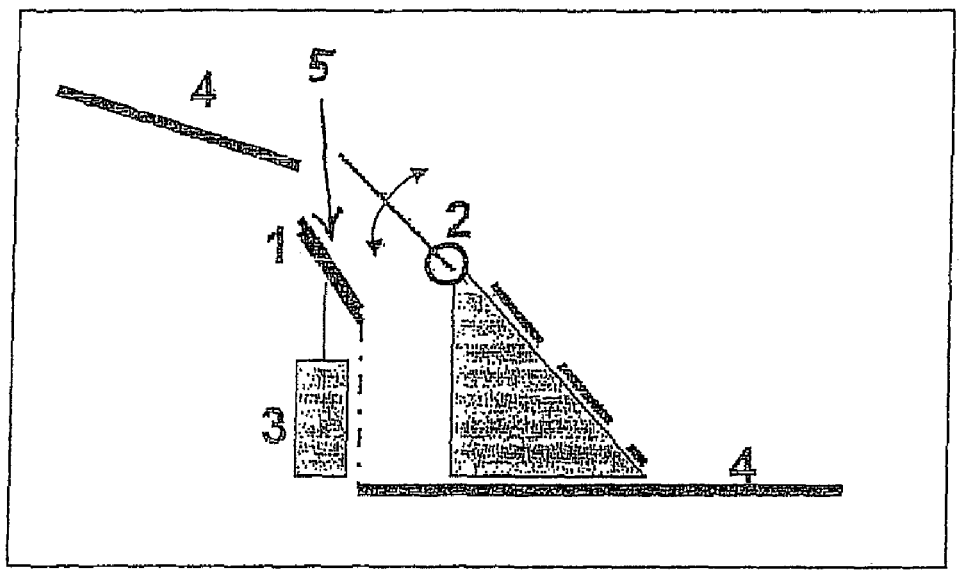

FIG. 3 describes the embodiment of the present invention in which a part of a flowing flow of the flowable material to be measured is diverted towards the measuring body by separating.

FIG. 4 clarifies the dependency of the dynamic viscosity of selected materials upon the temperature.

Figure 5:
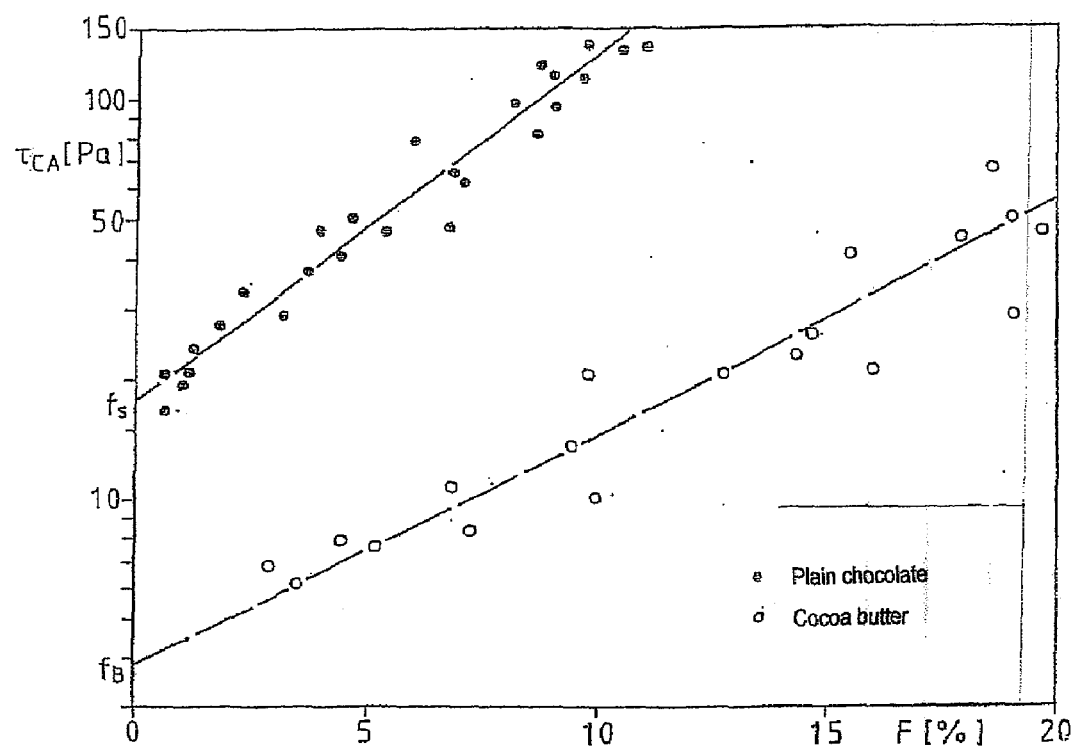

FIG. 5 shows, with reference to the examples of plain chocolate and cocoa butter, the effect of the content of fat crystals on the yield value.

A measuring body 1 with a defined surface is immersed periodically in a flowing mass 5 (e.g. chocolate mass) (FIG. 2) or is drenched periodically by this mass 4 (FIG. 3). After a certain contact time of the measuring body with the mass 5 or 4, the measuring body 1 is removed from the mass flow 5 or the mass supply 4 is interrupted. This takes place in the embodiment represented in FIG. 2 by withdrawing the measuring body 1 from the mass flow 5, in the embodiment represented in FIG. 3 by actuating a slide 2, by means of which the mass flow 4 is deflected. After freely flowing mass has discharged from the measuring body 1, the residual mass 2 (FIG. 2) or 5 (FIG. 3) still adhering is measured. The measurement is effected by determining the weight or volume of the mass layer 2 (FIG. 2) or 5 (FIG. 3) remaining on the measuring body 1, scales, a magnet, a force transducer or an oscillation sensor etc. being able to be used according to the solution route. From the adhering residual mass 2 (FIG. 2) or 5 (FIG. 3), the yield value can be calculated according to known laws of the inclined plane; these data are recorded electronically. The measurement is effected so rapidly that the mass remains unchanged during the measurement, i.e. that for example chocolate mass cannot be solidified by crystallisation.

As a result of repeated immersion or drenching, it is ensured that the adhering residual mass 2 (FIG. 2) or 5 (FIG. 3) from the preceding measurement is rinsed off again and a new measurement becomes possible. At the same time, the repeated immersion and withdrawal 4 (FIG. 2) or drenching serves, by actuation of a two-way valve, for periodic separating of a partial flow 2 (FIG. 3) for permanent tempering of the measuring body 1 to the current temperature of the mass. Periodic immersion 4 becomes possible due to a lifting mechanism 3 (FIG. 2), periodic drenching for example by the separating of a partial flow due to regular opening and closing of a valve 2 (FIG. 3). One advantage of this method is that the actual determination of the yield value is not disturbed by the flow process of the mass.

In the case of tempered chocolate masses, conclusions can be drawn about the tempering degree (i.e. the precrystallisation) from the measured yield value since this has a great effect on the yield value. This measurement of the tempering degree (=proportion of crystallised fat in the precrystallised, still flowable mass) is of particular importance since the tempering degree and flow behaviour of tempered masses can only be detected continuously with difficulty according to previous methods and are measured only rarely therefore in industrial practice.

COMPARATIVE EXAMPLE

Precrystallisation of Chocolates

Liquid chocolate mass has, according to the fat and cocoa content, typically a dynamic viscosity with an order of magnitude of 1 to 20 Pas. The chocolate melt passes through a tempering machine for precrystallisation in order to produce the first crystal nuclei in the fat phase with cooling and shearing. The thereafter precrystallised (=tempered) chocolate mass is only stable in the temperature range of approx. 27 to 33° C., with lower cooling it crystallises spontaneously, with further heating the crystal nuclei melt. Typically, the dynamic viscosity of a chocolate melt by way of example at a temperature of 34° C. is approx. 10 Pas; the yield value is at 20 Pa. This tempering is necessary for further processing and shaping of the chocolate mass. Precrystallised masses show, relative to the melt, a greatly altered flow behaviour. It was thus shown that precrystallised masses have substantially higher yield values (G. Ziegleder, M. Kegel, C. Santos, Fließverhalten vorkristallisierter Schokoladenmassen (Flow behaviour of precrystallised Chocolate Masses), ZSW 1990, 316-321; J. Kleinert, Rheologie der Schokolade (Rheology of chocolate), ZSW 28 (1975, 187-191). Rheological measurements on precrystallised masses in laboratory apparatus are difficult because of possible temperature differences since they change with a slight temperature deviation in their crucial property (content of fat crystals). The effect of the content of fat crystals on the yield value is represented in FIG. 5 with reference to the examples of plain chocolate and cocoa butter. A drastic increase in the yield value is detected with increasing crystal content. Masses also change during transport from the production plant to a laboratory since precrystallised masses (typical Theological measuring values at a temperature of 30° C.: dynamic viscosity: 15 Pas, yield value: 50 Pa) already develop a pronounced thixotropic behaviour during a short isothermal retaining time (G. Ziegleder, M. Kegel, C. Santos, Fließverhalten vorkristallisierter Schokoladenmassen (Flow behaviour of precrystallised Chocolate Masses), ZSW 1990, 316-321), i.e. increasing yield values develop and become more highly viscous. Hence the requirement for measuring yield value and viscosity on precrystallised or tempered masses during production becomes clear.

APPLICATION EXAMPLES

Table 2 shows yield values of molten chocolates and confectionery masses which were measured in a modern rheometer or calculated according to Casson and OICCC and, by comparison, yield values as were determined according to above-mentioned equations from the residual adhesion quantity on a vertical measuring body (or inclined plane). The relatively good correlation between OICCC data and measurement with reference to the inclined plane becomes clear.

TABLE 1

| Pas = kg/s · m | Dynamic viscosity [Pas] | Yield value [Pa] |
|---|---|---|
| Chocolate, molten | 0.1-20 | 0.1-30 |
| Cocoa butter molten | <1 | 0 |
| Chocolate, precrystallised | 10-50 | 20-100 |
| Cocoa butter precrystallised | 0-5 | 1-40 |
| Milk (0-160° C., 0-12% fat) | $4 \cdot 10^{-3}$ | — |
| Vegetable oil | $2\text{-}30 \cdot 10^{-3}$ | |
| | $2\text{-}30 \cdot 10^{-3}$ | |
| Confectionery masses | — | 10-100 |
| Tomato juice (dry substance temp.) | | |
| 0.01-0.4: 10% dry substance | | |
| 0.7-4.3: 25% dry substance | | |
| Milk | | |
| Cream | 0.8-1.5 | |
| Full milk | 18 | |
| Condensed milk, sugared | 12.550 | |
| Buttermilk | 16 | |
| Whey | 16 | |
| Mash | 1-300 | |
| Wine | 0.501-0.502 | |
| Biscuit dough | 11 | |
| Caramel mass | 18-950 | |
| Cocoa mass | 3-35 | |
| Syrup (20° C.) | 22-10.500 (according to dry substance) | |
| Body lotion | | |
| Cough mixture | | No yield value |
| Honey | 6-60 (according to moisture) | |
| Blood | $4 \cdot 10^{-3}$ | |
| Glycerine | 10 | |
| Water (20° C.) | $1 \cdot 10^{-3}$ | |
| Benzene | $0.6 \cdot 10^{-3}$ | |
| Castor oil | 1.06 | |
| Molasses | 150 | |
| Glass | $>10^{14}$ | |

TABLE 2

| | Yield value (Pa) at 40° C. | | |
|---|---|---|---|
| | Rheometer extrapolated, double determination | | Calculated from residual adhesion quantity/inclined |
| | OICCC/1 | OICCC/2 | plane |
| Milk chocolate | 19.85 | 20.38 | 21.1 |
| Plain chocolate | 33.14 | 36.31 | 33.4 |
| Cocoa butter | 0 | 0 | Not measurable |
| Filling material 1 | 43.34 | 44.64 | 42.0 |
| Filling material 2 | 49.81 | 49.04 | 47.9 |

The invention claimed is:

1. A method for measuring the yield value of flowable material in a flow of flowable material, comprising iteratively wetting a measuring body by the flowable material to be measured at a relatively constant temperature, subsequently permitting the flowable material to discharge for a discharge time so that the measuring body achieves approximately constant weight, and determining the yield value based upon the quantity of the flowable material adhering on the measuring body.

2. The method according to claim 1 wherein iteratively wetting a measuring body by the flowable material comprises sequentially and repeatedly immersing the measuring body in the flowable material and withdrawing the measuring body from the flowable material.

3. The method according to claim 2 further comprising at least one of selecting the time of immersion of the measuring body as a function of the viscosity of the flowable material to be measured to achieve at least one of substantially complete wetting of the measuring body and substantially complete exchange of the flowable material and calculating the time of immersion of the measuring body to achieve at least one of substantially complete wetting of the measuring body and substantially complete exchange of the flowable material.

4. The method according to claim 1 wherein iteratively wetting a measuring body by the flowable material comprises sequentially and repeatedly drenching the measuring body in the flowable material.

5. The method according to claim 4 further comprising at least one of selecting the time of drenching of the measuring body as a function of the viscosity of the flowable material to be measured to achieve at least one of substantially complete wetting of the measuring body and substantially complete exchange of the flowable material and calculating the time of drenching of the measuring body to achieve at least one of substantially complete wetting of the measuring body and substantially complete exchange of the flowable material.

6. The method according to claim 1 further comprising determining at least one of the weight and the volume of the quantity of the flowable material adhering on the measuring body after the discharge time.

7. The method according to claim 6 wherein determining at least one of the weight and the volume of the quantity of the flowable material adhering on the measuring body after the discharge time comprises at least one of: determining at least one of the weight and the volume of the quantity of the flowable material adhering on the measuring body with a scale; determining at least one of the weight and the volume of the quantity of the flowable material adhering on the measuring body with a force transducer; determining at least one of the weight and the volume of the quantity of the flowable material adhering on the measuring body with an oscillation sensor; determining at least one of the weight and the volume of the quantity of the flowable material adhering on the measuring body with an optical sensor; determining at least one of the weight and the volume of the quantity of the flowable material adhering on the measuring body with an electromagnetic sensor; determining at least one of the weight and the volume of the quantity of the flowable material adhering on the measuring body with a piezoelectric sensor; and, determining at least one of the weight and the volume of the quantity of the flowable material adhering on the measuring body with a pressure transducer.

8. The method according to claim 1 wherein iteratively wetting a measuring body by the flowable material to be measured comprises iteratively wetting at least one of vertical and inclined surfaces of the measuring body.

9. The method according to at claim 1 wherein iteratively wetting a measuring body by the flowable material to be measured at a relatively constant temperature, subsequently permitting the flowable material to discharge for a discharge time so that the measuring body achieves approximately constant weight, and determining the yield value based upon the quantity of the flowable material adhering on the measuring body comprises substantially maintaining in the adhering residual quantity the rheological properties to the flowable material from which it was removed.

10. The method according to claim 1 further comprising at least one of tempering the measuring body in the flowable material between two measuring cycles and rinsing the measuring body in the flowable material between two measuring cycles.

11. The method according to claim 1 further comprising at least one of further processing the thus-determined yield value data and electronically storing thus-determined yield value data.

12. The method according to claim 1 further comprising measuring the temperature of the flowable material.

13. A method for measuring the yield value of a dispersion in a flow of the dispersion, comprising iteratively wetting a measuring body by the dispersion to be measured at a relatively constant temperature, subsequently permitting the dispersion to discharge for a discharge time so that the measuring body achieves approximately constant weight, and determining the yield value based upon the quantity of the dispersion adhering on the measuring body.

14. A method for measuring the yield value of at least one of a food, a pharmaceutical, a cosmetic, a dispersion paint and a ceramic mass in a flow of the at least one of a food, a pharmaceutical, a cosmetic, a dispersion paint and a ceramic mass, comprising iteratively wetting a measuring body by the at least one of a food, a pharmaceutical, a cosmetic, a dispersion paint and a ceramic mass to be measured at a relatively constant temperature, subsequently permitting the at least one of a food, a pharmaceutical, a cosmetic, a dispersion paint and a ceramic mass to discharge for a discharge time so that the measuring body achieves approximately constant weight, and determining the yield value based upon the quantity of the at least one of a food, a pharmaceutical, a cosmetic, a dispersion paint and a ceramic mass adhering on the measuring body.

15. A method for measuring the yield value of at least one of a chocolate melt, yogurt, ketchup, sandwich spread, jam, honey, a cream, an ointment, a lotion and a lipstick in a flow of the at least one of a chocolate melt, yogurt, ketchup, sandwich spread, jam, honey, a cream, an ointment, a lotion and a lipstick, comprising iteratively wetting a measuring body by the at least one of a chocolate melt, yogurt, ketchup, sandwich spread, jam, honey, a cream, an ointment, a lotion and a lipstick to be measured at a relatively constant temperature, subsequently permitting the at least one of a chocolate melt, yogurt, ketchup, sandwich spread, jam, honey, a cream, an ointment, a lotion and a lipstick to discharge for a discharge time so that the measuring body achieves approximately constant weight, and determining the yield value based upon the quantity of the at least one of a chocolate melt, yogurt, ketchup, sandwich spread, jam, honey, a cream, an ointment, a lotion and a lipstick adhering on the measuring body.

16. A method for measuring the yield value and tempering degree of a chocolate melt in a flow of the chocolate melt, the method comprising iteratively wetting a measuring body by the chocolate melt to be measured at a relatively constant temperature, subsequently permitting the chocolate melt to discharge for a discharge time so that the measuring body achieves approximately constant weight, and determining the yield value based upon the quantity of the chocolate melt adhering on the measuring body.

17. A method for determining the tempering degree of a chocolate mass in a flow of chocolate mass, comprising iteratively wetting a measuring body by the chocolate mass at a relatively constant temperature, subsequently permitting the chocolate mass to discharge for a discharge time so that the measuring body achieves approximately constant weight, and determining the tempering degree based upon the quantity of chocolate mass adhering on the measuring body.

18. A device for the periodic measurement of the yield value of a flowable material, the device including a measuring body having a defined surface, a functional unit for determining a residual quantity of the flowable material which adheres to the measuring body after a discharge time, the measuring body in communication with the functional unit, and means for ensuring the periodic wetting of the measuring body with the flowable material.

19. The device according to claim 18 wherein the means for ensuring the periodic wetting of the measuring body with the flowable material comprises a device for lowering the measuring body into, and lifting the measuring body out of, the flowable material.

20. The device according to claim 18 wherein the means for ensuring the periodic wetting of the measuring body with the flowable material comprises a device for separating a partial quantity of the flowable material and for diverting the partial quantity to the measuring body.

21. The device according to claim 20 wherein the device for separating a partial quantity of the flowable material comprises at least one of a mechanical slide, a flap and a valve.

22. The device according to claim 18 wherein the measuring body comprises at least one of a rod, a plate, a funnel, a cone and a sphere.

23. The device according to claim 18 wherein the measuring body comprises at least one of vertical and inclined surfaces adapted to be wetted by the flowable material.

24. The device according to claim 18 wherein the functional unit for determining a residual quantity of the flowable material which adheres to the measuring body after a discharge time comprises at least one of a sensor for determining the weight of the flowable material which adheres to the measuring body after the discharge time, a sensor for determining the volume of the flowable material which adheres to the measuring body after the discharge time, a scale, a force transducer, an oscillation sensor, an optical sensor, an electromagnetic sensor, a piezoelectric sensor and a pressure transducer.

25. The device according to claim 18 further comprising an electronic evaluation unit for at least one of further processing the thus-determined yield value data and storing the thus-determined yield value data.

26. A method for continuous monitoring of the yield value of a flowable material in a production plant comprising operating a device including a measuring body having a defined surface, a functional unit for determining a residual quantity of the flowable material which adheres to the measuring body after a discharge time, the measuring body in communication with the functional unit, and means for ensuring the periodic wetting of the measuring body with the flowable material.

* * * * *